United States Patent [19]

Hempel

[11] Patent Number: 5,417,702
[45] Date of Patent: May 23, 1995

[54] SURGICAL CUTTING DEVICE

[75] Inventor: Sven Hempel, Kaltenkirchen, Germany

[73] Assignee: Ethicon, Inc., Somerville, N.J.

[21] Appl. No.: 110,591

[22] Filed: Aug. 23, 1993

[30] Foreign Application Priority Data

Aug. 28, 1992 [DE] Germany .................. 42 28 910.6

[51] Int. Cl.⁶ ................................................ A61B 17/00
[52] U.S. Cl. ................................... 606/151; 606/157; 606/170
[58] Field of Search ............. 606/213, 215, 139, 144, 606/148, 151, 157, 170, 167, 182, 232

[56] References Cited

U.S. PATENT DOCUMENTS

| | | | |
|---|---|---|---|
| 4,648,415 | 3/1987 | Yuan ........................... | 132/73 |
| 4,847,994 | 7/1989 | Dunn ........................... | 30/28 |
| 5,196,022 | 3/1993 | Bilweis ........................ | 606/144 |
| 5,242,459 | 9/1993 | Buelna ........................ | 606/148 |

FOREIGN PATENT DOCUMENTS

| | | | |
|---|---|---|---|
| 0534696 | 3/1993 | European Pat. Off. .......... | 606/213 |
| 0912619 | 5/1954 | Germany ....................... | 606/139 |

*Primary Examiner*—Stephen C. Pellegrino
*Assistant Examiner*—Jeffrey A. Schmidt
*Attorney, Agent, or Firm*—Paul A. Coletti

[57] ABSTRACT

A cutting device for a surgical instrument, especially for a laparoscopic instrument, for the cutting of binding element, such as ligature binders, surgical suture material, etc. or of other objects is described, the end-piece which is to be out off of the object being drawn in by the instrument until a thicker section of the object, such as the headpiece of a ligature binder or a knot in surgical suture materials, etc., reaches the vicinity of the instrument head. The cutting device has a cutting part arranged at the instrument head, the cutting edge of the cutting part being moved essentially transversely through the end-piece by an actuation part engaging at the thicker section upon the continued drawing-in of the end-piece which is severed when a pre-set force is exceeded.

4 Claims, 2 Drawing Sheets

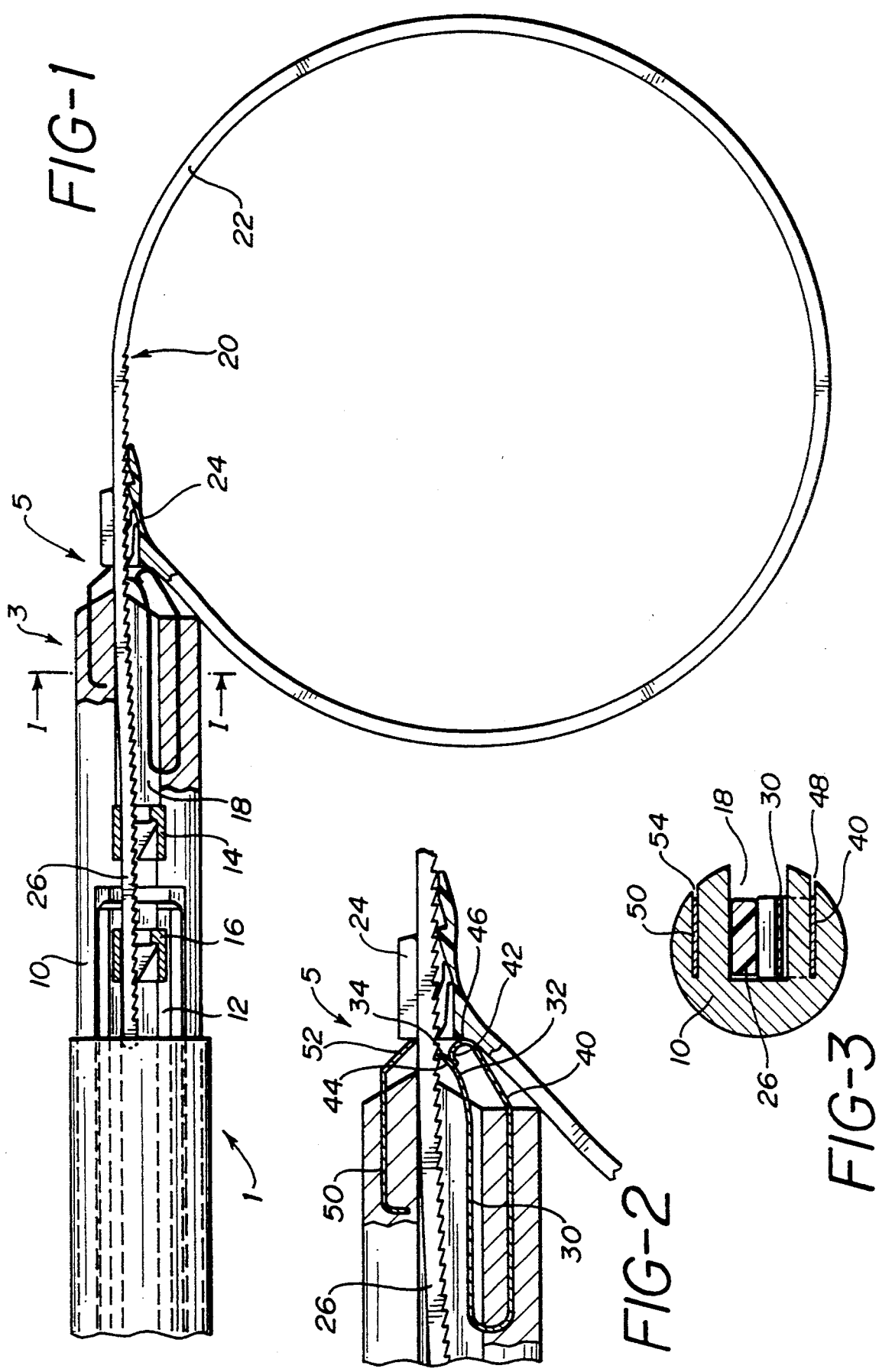

SURGICAL CUTTING DEVICE

RELATED APPLICATION

This application is based on German application No. P4228910.6 filed Aug. 28, 1993.

FIELD OF THE INVENTION

The invention relates to a cutting device for a surgical instrument.

BACKGROUND OF THE INVENTION

There are surgical instruments in which the end-piece of a surgical object is drawn into the instrument during the course of an operation, until a thicker section of this object reaches the vicinity of an instrument head, whereupon the need arises to sever the end-piece of the object at the instrument head. Such instruments are used, in particular in minimally invasive surgery and in laparoscopy.

The surgical objects may be binding elements such as ligature binders or surgical suture material. There is for example a laparoscopic instrument which is introduced through a cannula (trocar sleeve) into the inside of the body, having a stretched ligature binder laid about an organ to be ligated, and transformed into a closed shape through insertion of its headpiece into its binding part. The end-piece of the ligature binder is then drawn into the inside of the instrument.

First, the headpiece of the ligature binder representing a thicker section, lays itself against the instrument head. Second, as the drawing-in of the end-piece continues, the binding part glides in the headpiece, whereupon the ligature binder narrows more and more. Third, a movement in an opposite direction is prevented by a pawl arranged in the headpiece, which pawl engages a toothing to which the binding part is provided. Finally, the ligature binder lies tightly enough about the organ. The end-piece of the binding part must now be cut off at the headpiece of the ligature binder. If a separate cutting instrument is used for this, having for example been introduced into the inside of the body through another cannula, this is awkward, and there is the risk of making the cut in the wrong place.

Known from WO 09/06725 is a laparoscopic instrument for the looping about of hollow organs and laying of endoligatures, which is introducible into the abdominal area through a cannula. In the case of this instrument, the base body of a ligature binder is fitted onto the distal end of the instrument head. The base body is provided with a continuous channel which runs in longitudinal direction of the instrument head. A belt-like, loop-shaped continuation connects with the distal end of the base body. The free end of the continuation is grasped by the operator with an additional auxiliary aid, laid about the organ which is to be ligated, and introduced into the channel. The free end of the belt-like continuation and the channel are provided with notched surfaces which correspond to each other and which prevent a release or loosening of the connection. On the inside of the instrument, the free end can be grasped by a gripping tool which is movable in longitudinal direction, in order to pull the ligature binder tight. In order to cut off the end-piece of the belt-like continuation in the inside of the instrument, a blade is provided which is to be actuated by the operator via the instrument shaft. Although this facilitates severance, the operator has no idea as to how tightly the ligature binder is lying about the organ. If it is sitting too tightly, this can have disadvantageous consequences for the organ; of it is sitting too loosely, it can become detached. This cannot be appraised with certainty by means of a visual inspection.

SUMMARY OF THE INVENTION

It is an object of the invention to provide a cutting device for a surgical instrument, with whose help the operational procedure is simplified and which prevents the surgical object which is to be cut off from sitting too tightly or too loosely after severance.

This is achieved through a cutting device for surgical instrument as described herein. Arranged at the instrument head is a cutting part whose cutting edge is coupled to an actuation part and is essentially transversely movable through the end-piece which is to be cut off. The cutting-off is automatic when the end-piece is drawn in, and it is not necessary to introduce a separate cutting instrument from outside, e.g., through another cannula. The cutting process takes place only when a preset force on the object exceeded. The result of the instrument with a well defined force, namely until the end-piece is severed. It therefore sits neither too tightly nor too loosely about the looped and ligated organ.

In an advantageous version, the cutting part and the actuation part are designed as leaf springs which define the force at which the cutting device operates. This design is inexpensive, especially if the two leaf springs are connected to each other in one piece, and is thus well suited for use with disposable articles. Further, a spring element can also be provided for defining the force at which the cutting process takes place.

In a further advantageous version, the actuation part is a component guided in the instrument head displaceable in the direction of the axis of the instrument head. The component projects outwards from the instrument head and has an aperture through which the end-piece which is to be cut off is drawn into the instrument. The actuation part is pre-tensioned outwards by the force of a spring. The spring is preferably adjustable, so that the operator can individually match the force which occurs during the cutting process to the patient and organ. The actuation part can engage at the cutting part via a curved guide. The guiding of the actuation part in the instrument head ensures a balanced transmission of force from the thicker section onto the cutting part, thereby avoiding a tilting which could otherwise occur, especially if the thicker section is irregularly structured and engages a symmetrically at the actuation part.

DESCRIPTION OF THE DRAWINGS

The invention is described in more detail below with reference to the drawings, which show:

FIG. 1 a longitudinal section through an instrument head, providing with a first embodiment of the cutting device according to the invention, of a laparoscopic instrument for the laying of endoligatures, the headpiece of an already closed ligature binder being brought against the instrument head, FIG. 2 a magnified segment from FIG. 1 which shows the details of the cutting device, FIG. 3 a cross-section along the line I—I from FIG. 1, and FIG. 4 a longitudinal section through another embodiment of the cutting device according to the invention.

DETAILED DESCRIPTION OF THE INVENTION

Figure 4:
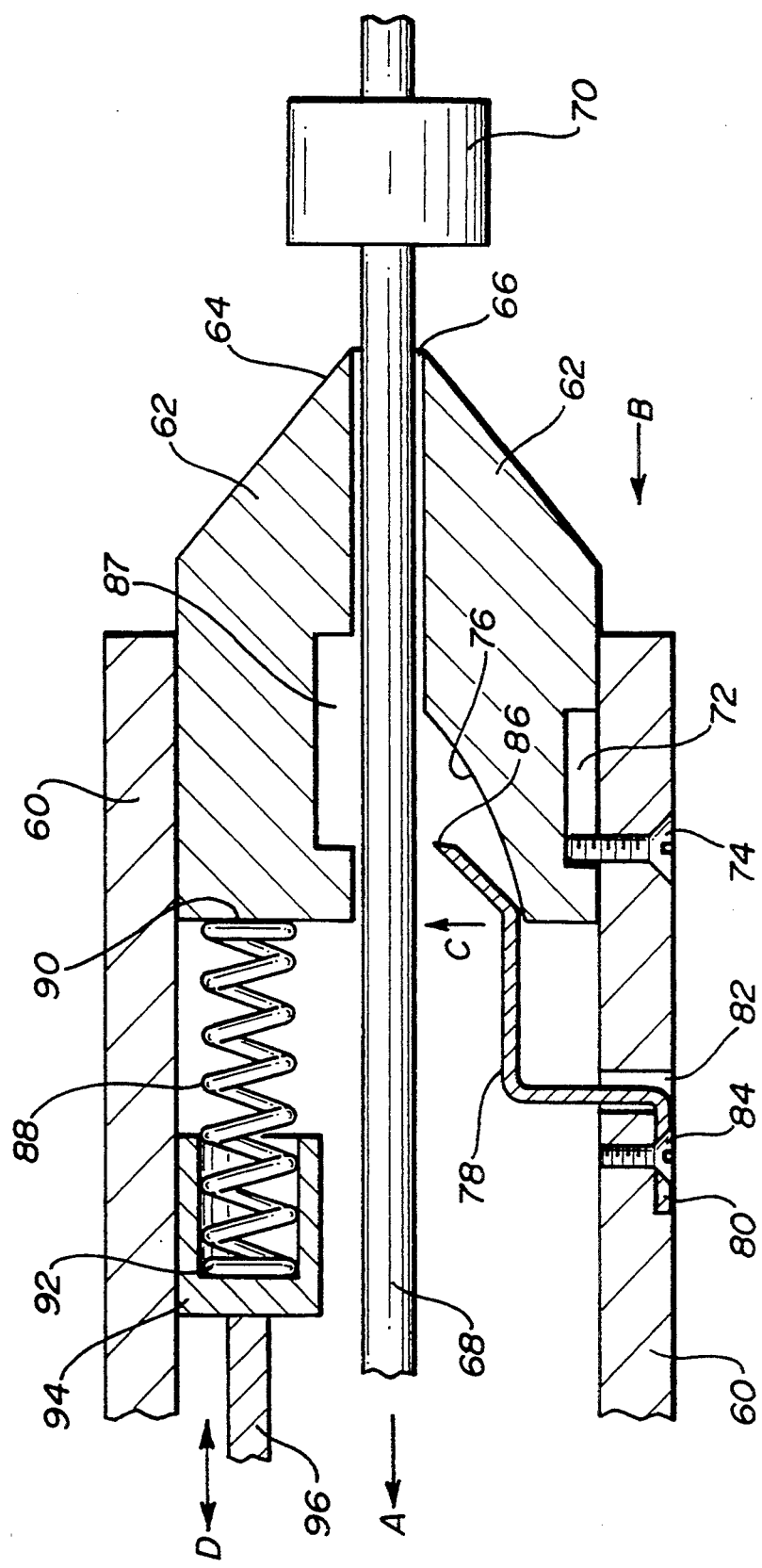

FIG. 1 shows the front or distal zone of a laparoscopic instrument 1 which zone is designed as an instrument head 3. The instrument head 3 carries a cutting device 5 according to the present invention.

An actuation rod 12 is guided in longitudinally displaceable manner in a shaft 10 of the instrument 1. The shaft 10 carries a front ratchet head 14, while a rear ratchet head 16 is secured to the actuation rod 12. A lateral recess 18 runs between the ratchet heads 14, 16 and as far as the distal end of the instrument head 3, see also FIG. 3.

A ligature binder 20 is inserted into the instrument 1. The ligature binder 20 comprises a flexible binding part 22 which is provided on one side with teeth, and a headpiece which contains a pawl which is matched to the teeth of binding part 22. When the ligature binder 20 is closed, as shown in FIG. 1, so that binding part 22 is inserted into headpiece 24, the ligature binder 20 can be pulled into an ever narrower shape. An opening is prevented by the cooperation between the pawl in the headpiece 24 and the teeth at binding part 22. The zone at the free end of binding part 22, namely the end-piece 26 which is to be cut off, is placed in the lateral recess 18 in the instrument head 3 and guided through the two ratchet heads 14, 16.

In order to draw the end-piece 26 which is to be cut off further into the instrument, the actuation rod 12 is moved to the left. The rear ratchet head 16 which, like the front ratchet head 14, has a similar structure to headpiece 24, locks and takes along the end-piece 26 which is to be cut off. During this process, the end-piece 26 which is to be cut off can glide through the front ratchet head 14 and through the headpiece 24, no noteworthy force being exerted on the distal end of the instrument head 3. With the instrument 1 which is represented, the actuation rod 12 can be moved only within a small range. It must therefore be pushed back to the right, whereupon the front ratchet head 14 locks, while the end-piece 26 which is to be cut off glides through the rear ratchet head 16. Upon repetition of the movement of the actuation rod 12, the end-piece 26 which is to be cut off is gradually drawn ever further into the inside of the instrument 1, until it lies against the looped organ, e.g. a blood vessel or a hollow organ which is laid over the shaft of the counter-support (anvil) of a circular clip suture apparatus. As the drawing-in of the end-piece 26 which is to be cut off continues, i.e. as the tightening of the ligature binder 20 continues, the force increases rapidly and the cutting device 5 according to the invention is actuated.

FIG. 2 shows the details of the cutting device 5. A cutting part 30 is designed as a leaf spring. Its distal end-zone 32 is curved upwards, i.e. onto the end-piece 26 which is to be cut off of the ligature binder 20, and sharpened to a cutting edge 34.

An actuation part 40 is likewise designed as a leaf spring whose distal end-zone is shaped into an engagement piece 42. The proximal side 44 of the engagement piece 42, i.e. the side pointing to the instrument head 1, lies against the curved end-zone 32 of the cutting part 30. The distal side 46 of the engagement piece 42 engages at the headpiece 24 of the ligature binder 20 which represents a thicker section.

The cutting part 30 and the actuation part 40 are preferable connected to each other in one piece. Securing at the instrument head 3 takes place with the help of a slot 48 into which the actuation part 40 is inserted, see FIG. 3. Provided at the instrument head 3 on the other side of the end-piece 26 which is to cut off is further spring element 50 which is preferable likewise designed as a leaf spring and inserted into a slot 54. An angled end-zone 52 of the further spring element 50 lies against the headpiece 24.

When, compared with the situation represented, the end-piece 26 which is to be cut off is drawn further into the instrument 1, the headpiece 24 forces the engagement piece 42 to the left, whereupon the letter pushes the curved end-zone 32 likewise to the left. Because of its curved shape, this end-zone can only escape upwards, so that the cutting edge 34 formed at its end travels essentially transversely through the end-piece 26 which is to be cut off until the latter is severed. At the same time, the lateral recess 18 prevents the escape of the end-piece 26 which is to be cut off.

The force with which the cutting process takes place is fixed by the spring action of the cutting part 30, of the actuation part 40 and of the further spring element 50. The further spring element 50 can thus serve to tune the force, e.g., by using a standard spring for the unit consisting of the cutting part 30 and the actuation part 40, while the further spring element 50 is selected with respect to its strength according to the force to be applied for the individual case in question. The further spring element 50 also prevents tilting of the headpiece 24 when the ligature binder 20 tightens, since the further spring element 50 and the engagement piece 42 together act with largely symmetrical force on the headpiece 24.

The cutting device 5 according to the embodiment which is represented has a simple structure, for which reason it can be manufactured together with the shaft 10 of the instrument 1 as a disposable article.

FIG. 4 shows a further embodiment of the cutting device according to the invention. An actuation part 62 is housed longitudinally displaceable in a housing 60 of the instrument head. The front end 64 of the actuation part 62 ends in the shape of a cone and is provided at its distal end with an aperture 66 through which the end-piece 68, which is to be cut off when a predetermined force is reached, of an object is introduced into the inside of the instrument. A thicker section 70 of this object is already brought tightly up against the front end 64.

In a region adjacent to the inside wall of the housing 60, the actuation part 62 is provided with an elongated opening 72 into which a screw 74, driven through the wall of the housing 60, engages. Through the combination of opening 72 and screw 74, a rotation of the actuation part 62 in relation to the housing 60 is prevented; at the same time, the displacement range of the actuation part 62 is fixed.

A curved guide 76 at the actuation part 62 engages at a cutting part 78 which is designed as a leaf spring. Its end 80 is guided through an aperture 82 in the wall of the housing 60 and secured on the outside by a screw 84. At the other end, a cutting edge 86 is angled off from the cutting part 78. Opposite to the cutting edge 86 and optionally offset in distal direction, the actuation part 62 has a recess 87 which is wide enough to accommodate the cutting edge 86.

A compression spring 88 lies with its distal end 90 against the actuation part 62, while its proximal end 92 is housed in a casing 94. The longitudinal alignment of the casing 94 can be adjusted, with the help of a guide and adjustment apparatus 96 which is only roughly sketched in FIG. 4, both in proximal and distal direction as indicated by the two-way arrow D in FIG. 4. The force with which the cutting process takes place can be fixed by adjusting the position of the casing 94 (which step can be performed for example with the help of a spindle or of a "Bowden" wire) and also from the handle of the surgical instrument. If the casing 94 is moved to the right, i.e. in distal direction, the compression spring 88 is more tightly compressed, and the force is greater, than when the casing 94 is moved to the left, i.e. in proximal direction.

The cutting process with the help of the inventive cutting device according to the embodiment represented in FIG. 4 proceeds as follows: With the help of the instrument, the end-piece 68 which is to be cut off is moved in the direction of the arrow A. This required only a little force, until the thicker section 70 lies against the front end 64 of the actuation part 62. However, the force can also still be small thereafter, e.g., if the end-piece 68 which is to be cut off is the end-piece of a loop which is drawn through the thicker section 70 but does not yet lie against an organ. Only as soon as this is the case does the force rapidly increase. As soon as it is greater than the force exerted by the compression spring 88, the actuation part 62 is moved in the direction of the arrow B upon the further drawing-in of the end-piece 68 which is to be cut off. The cutting part 78 glides along the curved guide 76, so that the cutting edge 86 is guided essentially in the direction of the arrow C until finally it has severed the end-piece 68 which is to cut off. When the cutting part 78 is at its most deflected position, the cutting edge 86 lies in the recess 87. As soon as the end-piece 68 which is to be cut off is cut through, the thicker section 70 can no longer exert force on the actuation part 62. The compression spring 88 then pushes the actuation part 62 back into its distal position, whereupon the cutting edge 86 likewise reverts to its starting position as a result of the spring action of the cutting part 78.

This embodiment is of a more complex design than that described previously, but it does make possible an individual setting of the force exerted by the compression spring 88. Although the compression spring 88 does not engage centrally, the actuation part 62 does not tend to tilt, as it is securely guided in the housing 60. The symmetrical configuration of the front end 64 permits a reliable application, even when the thicker section 70 is very irregular in shape.

I claim:

1. In combination:
    a surgical instrument having an instrument head containing a cutting device for the cutting of a binding element;
    a binding element having an end-piece and a thicker section attached to the end-piece, the end-piece of said element which is to be cut off by said cutting device, said end-piece being drawn into said instrument until a predetermined section of said element has reached the vicinity of said instrument head;
    and said cutting device characterized in that said cutting device comprises:
    a cutting edge on said instrument head, said cutting edge being automatically movable essentially transversely through the end-piece, when a pre-set force on said cutting device exerted by said binding element is exceeded; and
    an actuation part on said instrument head engaging said predetermined section of said binding element; and
    characterized in that the cutting device is designed as a first leaf spring whose end-zone is curved towards the end-piece which is to be cut off and is sharpened to a cutting edge, and that the actuation part is a second leaf spring with an engagement piece arranged at its end, the side of the engagement piece which points to the instrument head lying against the curved end-zone of the first leaf spring and being engageable by the thicker section, the engagement piece curving the curved end-zone of the first leaf spring against the forces exerted by the first and second leaf spring.

2. Cutting device according the claim 1, characterized in that at least one further spring element is attached to said instrument head, and being engageable by the thicker section and deformable under expenditure of force, in order, together with the first and second leaf spring, to define said pre-set force.

3. Cutting device according to claim 2, characterized in that the further spring element is an angled leaf spring.

4. Cutting device according to claim 1 characterized in that the first and the second leaf spring are connected to each other in one piece.

* * * * *